United States Patent [19]

Huth et al.

[11] Patent Number: 4,933,345
[45] Date of Patent: Jun. 12, 1990

[54] ISOXAZOLE-β-CARBOLINE DERIVATIVES

[75] Inventors: Andreas Huth; Dieter Rahtz; Ralph Rohde; Ralph Schmiechen; Dieter Seidelmann; Herbert Schneider; David N. Stephens, all of Berlin, Fed. Rep. of Germany; John B. Hansen, Lyngby, Denmark; Mogens Engelstoft, Vaerlose, Denmark; Preben Olsen, Copenhagen, Denmark

[73] Assignee: Schering Aktiengesellschaft, Berlin and Bergkamen, Fed. Rep. of Germany

[21] Appl. No.: 237,368

[22] Filed: Aug. 29, 1988

[30] Foreign Application Priority Data

Aug. 28, 1987 [DK] Denmark .............................. 4498/87
Sep. 9, 1987 [DE] Fed. Rep. of Germany ....... 3730667

[51] Int. Cl.$^5$ ................ A61K 31/435; A61K 31/495; C07D 471/04; C07D 417/12
[52] U.S. Cl. .................... 514/253; 514/228.2; 514/232.8; 514/254; 514/269; 514/272; 514/274; 514/292; 544/60; 544/121; 544/238; 544/298; 544/300; 544/310; 544/316; 544/317; 544/319; 544/320; 544/321; 544/405; 544/361; 546/15; 546/86; 546/87
[58] Field of Search ............... 546/15, 86, 87; 544/60, 544/126, 361, 298, 300, 310, 316, 317, 319, 320, 321, 238, 405; 514/292, 228.2, 232.8, 269, 272, 274, 253, 254

[56] References Cited

FOREIGN PATENT DOCUMENTS 0054507 6/1982 European Pat. Off. ............ 546/86
0130140 1/1985 European Pat. Off. ............ 546/86
0218541 4/1987 European Pat. Off. ............ 546/86
0237467 9/1987 European Pat. Off. ............ 546/86

OTHER PUBLICATIONS

Danish Patent Application No. 913/81, filed Feb. 27, 1981.

Primary Examiner—Mary C. Lee
Assistant Examiner—J. Richter
Attorney, Agent, or Firm—Millen, White & Zelano

[57] ABSTRACT

β-Carbolines of general Formula I

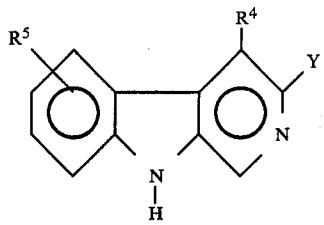

wherein
Y represents the residue

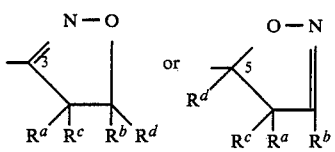

and $R^a$ and $R^b$, being identical or different, mean respectively hydrogen, $C_{1-6}$-alkoxy, phenyl, $C_{3-7}$-cyclo-alkyl, optionally substituted $C_{1-6}$-alkyl or $C_{1-6}$-alkoxycarbonyl, and $R^c$ and $R^d$, being identical or different, mean respectively hydrogen or $C_{1-6}$-alkyl or jointly a linkage, and
$R^4$ is hydrogen, $C_{1-6}$-alkyl or $C_{1-6}$-alkoxy-$C_{1-6}$-alkyl and
$R^5$ is hydrogen, halogen, $OR^6$, $NR^7R^8$ or $CH R^9R^{10}$ wherein $R^6$ means $C_{1-6}$-alkyl, $C_{3-7}$-cycloalkyl or an optionally substituted aralkyl, aryl or hetaryl residue, $R^7$ and $R^8$, being identical or different, represent hydrogen, $C_{1-6}$-alkyl, $C_{3-6}$-alkenyl, or jointly with the nitrogen atom a saturated heterocyclic five- or six-membered ring which optionally contains a further hetero atom, $R^9$ means hydrogen or $C_{1-6}$-alkyl, $R^{10}$ means hydrogen, $C_{1-6}$-alkyl, $OR^{11}$ or $NR^{12}R^{13}$ wherein $R^{11}$ means $C_{1-6}$-alkyl, $R^{12}$ and $R^{13}$ are identical or different and mean hydrogen, $C_{1-6}$-alkyl or jointly with the nitrogen atom a saturated heterocyclic five- or six-membered ring optionally containing a further hetero atom, are useful to treat epilepsy or anxiety.

17 Claims, No Drawings

ISOXAZOLE-β-CARBOLINE DERIVATIVES

BACKGROUND OF THE INVENTION

The invention relates to novel β-carboline derivatives substituted in the 3-position by isoxazole or isoxazoline derivatives, a process for their preparation, and their use as medicinal agents.

EP-A No. 54,507 describes β-carbolines substituted in the 3-position by the isoxazolone residue. These compounds show low affinity for the benzodiazepine receptors.

It has now been found that the β-carbolines according to this invention which are substituted in the 3-position by isoxazole or isoxazoline residues surprisingly exhibit a high specific affinity for benzodiazepine receptors in that they displace radioactively labeled flunitrazepam from the benzodiazepine receptors.

SUMMARY OF THE INVENTION

One aspect of this invention is to provide novel isoxazole-β-carboline derivatives.

Another aspect of this invention is to provide pharmaceutical compositions, especially for treating disorders of the central nervous system, containing these compounds.

A third aspect of this invention is a process for making these compounds.

Upon further study of the specification and appended claims, further objects and advantages of this invention will become apparent to those skilled in the art.

DETAILED DISCUSSION

The compounds of this invention have the general Formula I

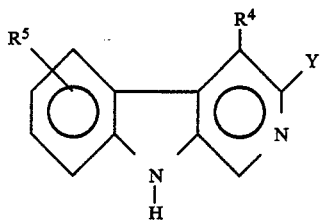

wherein
Y represents the residue

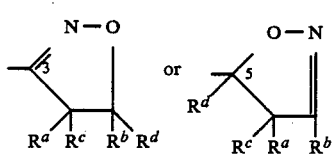

and $R^a$ and $R^b$, being identical or different, mean respectively hydrogen, $C_{1-6}$-alkoxy, $C_{3-7}$-cycloalkyl, phenyl, optionally substituted $C_{1-6}$-alkyl or $C_{1-6}$-alkoxycarbonyl, and $R^c$ and $R^d$, being identical or different, mean respectively hydrogen or $C_{1-6}$-alkyl or jointly a linkage, and $R^4$ is hydrogen, $C_{1-6}$-alkyl or $C_{1-6}$-alkoxy-$C_{1-6}$-alkyl, and
n is 1 or 2, $R^5$ is hydrogen, halogen, $OR^6$, $NR^7R^8$ or $CHR^9R^{10}$ wherein $R^6$ means $C_{1-6}$-alkyl, $C_{3-7}$-cycloalkyl or an optionally substituted aralkyl, aryl or hetaryl residue, $R^7$ and $R^8$, being identical or different, represent hydrogen, $C_{1-6}$-alkyl, $C_{3-6}$-alkenyl, or jointly with the nitrogen atom a saturated heterocyclic five- or six-membered ring which optionally contains a further hetero atom, $R^9$ means hydrogen or $C_{1-6}$-alkyl, $R^{10}$ means hydrogen, $C_{1-6}$-alkyl, $OR^{11}$ or $NR^{12}R^{13}$ wherein $R^{11}$ means $C_{1-6}$-alkyl, $R^{12}$ and $R^{13}$ are identical or different and mean hydrogen, $C_{1-6}$-alkyl or jointly with the nitrogen atom a saturated heterocyclic five- or six-membered ring optionally containing a further hetero atom.

The substituent $R^5$ can be present singly or doubly in the 5-, 6-, 7- and/or 8-positions, the substitution in the 5- or 6-position being preferred.

$C_{1-6}$-alkyl and $C_{1-6}$-alkyl portions of all other groups herein, represent in each case a straight or branched alkyl group of 1-6 carbon atoms; examples that can be cited are methyl, ethyl, propyl, ispropyl, butyl, secbutyl, tertbutyl, isobutyl, pentyl and hexyl; $C_{1-4}$-alkyls are to be considered preferred.

If $R^4$ means an alkoxyalkyl group, then $C_{1-4}$-alkoxy-$C_{1-2}$-alkyl is to be considered prerferred.

Examples of cycloalkyl residues $R^a$, $R^b$, $R^c$ and $R^6$ are cyclopropyl, cyclobutyl, cyclopentyl, cyclohexyl and cycloheptyl.

Suitable substituents for the alkyl residues $R^a$ and $R^b$ include hydroxy, $C_{1-6}$-alkoxy, preferably $C_{1-4}$-alkoxy, phenyl, or halogen; in particular, $CH_2OH$, $CH_2$—O—$C_{1-4}$-alkyl, and benzyl can be cited as examples of substituted alkyl residues $R^a$ and $R^b$.

Halogen is understood to mean in all cases fluorine, chlorine, bromine or iodine, wherein chlorine and bromine are preferred.

The aralkyl residue $R^6$ can contain 7-10 carbon atoms (typically 6-10 in the aryl group) and can be linear or branched in the alkyl residue. Preferred are Ar—$C_{1-2}$-alkyls which can optionally be substituted once or twice in the aryl residue. Preferred are Ar—$C_{1-2}$-alkyls which can optionally be substituted once or twice in the aryl residue. Suitable substituents in the aralkyl residue are, for example, halogen, $C_{1-4}$-alkoxy, $C_{1-4}$-alkyl, or amino. Ar—$C_{1-2}$-alkyls are preferred; these can be substituted in the aryl residue by 1-2 halogens, such as, for example, benzyl, phenethyl, α-methylbenzyl, 4-chlorophenethyl, 3-bromobenzyl, etc.

Aryl residues $R^6$ can have 6-10 carbon atoms and can optionally be mono- to disubstituted, e.g., by halogen, nitro, cyano, $C_{1-4}$-alkyl or $C_{1-4}$-alkoxy. Phenyl, 2-chlorophenyl, 4-chlorophenyl, 2,4-dichlorophenyl, 2-nitrophenyl and 2-cyanophenyl can be cited as being preferred.

In case $R^6$ means a heteroaromatic residue, then the latter can be 5- or 6-membered and can be optionally be mono- or trisubstitued. Suitable substituents of the heteryl residue are the substituents recited for the aryl residue $R^6$. The heteroaromatic can contain one or two hetero atoms, such as sulfur, nitrogen and/or oxygen.

6-membered ring heteroaromatics with 1 to 2 nitrogen atoms and 5-membered ring heteroaromatics with 1 to 2 oxygen, sulfur and/or nitrogen atoms which can be substituted by halogen are preferred, such as, for example, pyridine, pyrimidine, pyrazine, pyridazine, furan, thiophene, pyrrole, imidazole, thiazole. In particular, preferred residues that can be cited are pyridine, pyrimidine, pyridazine, pyrazine, and 5-bromopyridine.

In case $R^7$, $R^8$ and $R^{12}$, $R^{13}$ form jointly with the nitrogen atom a saturated heterocyclic five- or six-membered ring optionally containing a further hetero atom, then such ring represents, for example, pyrrolidine, piperidine, morpholine, piperazine or thiomorpholine and can, if desired, be substituted with one to two $C_{1-4}$-alkyl groups, such as, for example, 2,6-dimethyl-morpholine or N-methylpiperazine.

Examples of alkenyl residues $R^7$ and $R^8$ are allyl and butenyl.

The novel compounds of general Formula I are pharmacologically effective substances distinguished, inter alia, by an effect on the central nervous system and suitable especially as psychopharmaceuticals for mammalian, especially human medicine. Since the compounds of this invention exhibit not only a high specific affinity to the benzodiazepine receptors but also show a very low toxicity, they display an especially favorable thereapeutic index. At the same time, metabolic stability is markedly improved over the known β-carbolines. Based on the surprisingly good efficacy in the PTZ convulsion test, the compounds of this invention are particularly suitable for the treatment of epilepsy and anxiety.

The compounds of the invention can be utilized for the formulation of pharmaceutical preparations, e.g. for oral and parenteral administration, in accordance with conventional methods of galenic pharmacy.

Suitable auxiliary agents for formulating pharmaceutical preparations are those physiologically compatible organic and inorganic excipients for enteral and parenteral use which are inert with respect to the compounds of this invention.

Examples of excipients are: water, saline solutions, alcohols, polyethylene glycols, polyhydroxyethoxylated castor oil, gelatin, lactose, amylose, magnesium stearate, talc, silicic acid, fatty acid mono- and diglycerides, pentaerythritol fatty acid esters, hydroxymethylcellulose, and polyvinylpyrrolidone.

The pharmaceutical preparations can be sterilized and/or combined with auxiliary agents such as lubricants, preservatives, stabilizers, wetting agents, emulsifiers, buffers, and colorants.

Especially suitable for parenteral administration are injection solutions or suspensions, particularly aqueous solutions of the active compounds in polyhydroxyethoxylated castor oil.

Usable excipient systems are also surfactant auxiliary agents, such as salts of the bile acids or animal or vegetable phospholipids, but also mixtures thereof, as well as liposomes or their components.

Especially suited for oral administration are tablets, dragees or capsules with talc and/or a hydrocarbon vehicle or binder, e.g., lactose, cornstarch or potato starch. Use can also take place in liquid form, e.g., as an elixir optionally with added sweetener.

The compounds of this invention are administered in a dosage unit of 0.05–100 mg of active compound in a physiologically acceptable vehicle.

The compounds of this invention are utilized in a dose of 0.1–300 mg per day, preferably 0.1–30 mg per day, particularly preferably 1–20 mg per day. They can be used to treat epilepsy and axiety analogously to the known agents valproate and diazepam, respectively.

The compounds according to this invention are prepared in accordance with methods known per se.

For example, the compounds of general Formula I can be produced by (a) cyclizing nitrile oxides of general Formula II

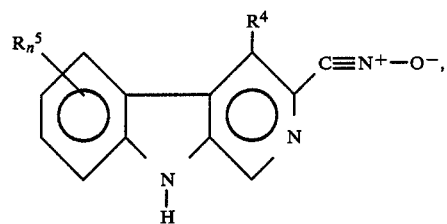

wherein $R^4$, $R^5$ and n have the meanings recited above, with a compound of general Formula III

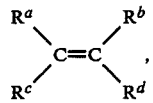

wherein $R^a$, $R^b$, $R^c$ and $R^d$ have the meanings given above; to compounds of general Formula I wherein Y means

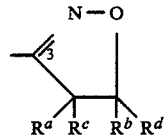

$R^a$, $R^b$, $R^c$ and $R^d$ having the above-indicated meanings; or (b) cyclizing nitrile oxides of general Formula IV

wherein $R^b$ has the meanings given above, with compounds of general Formula V

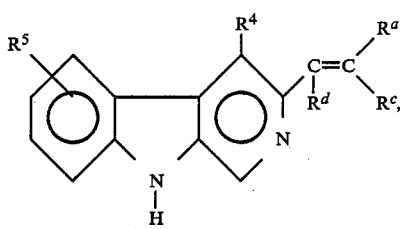

wherein $R^a$, $R^c$, $R^d$, $R^4$ and $R^5$ have the meanings set forth above, to compounds of general Formula I wherein Y means

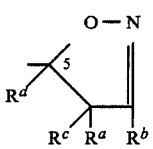

wherein $R^a$, $R^b$, $R^c$ and $R^d$ have the meanings set forth above; or (c) reacting compounds of general Formula VI

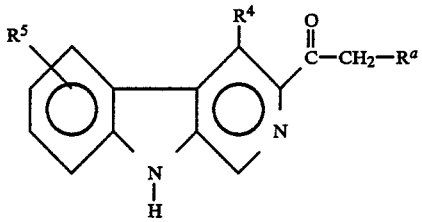

wherein $R^a$, $R^4$ and $R^5$ have the meanings given above, to the enaminone and cyclizing the latter with hydroxylamine—O—sulfonic acid to compounds of general Formula I wherein Y means

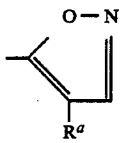

wherein $R^a$ has the meanings set forth above.

The cycloaddition of the compounds of general Formulae II and IV takes place at temperatures of 0°–40° C. in an aprotic solvent and is generally finished after 4–20 hours. Suitable aprotic solvents are aliphatic and cyclic ethers, such as diethyl ether, tetrahydrofuran, dioxane, halogenated hydrocarbons, such as dichloroethane, methylene chloride, chloroform, hydrocarbons, such as hexane, pentane, and dimethylformamide, dimethyl sulfoxide, etc.

If the starting compounds are gaseous, such as acetylene, for example, then it is advantageous to utilize in the reaction corresponding liquid compounds containing a group that can be readily split off afterwards. Suitable as a group that is readily split off is the trialkylsilyl group, for example.

The splitting-off step is conducted prior to working up the reaction mixture in accordance with the conventional methods, such as, for example, by adding bases at room temperature. Suitable bases are, for example, alkali hydroxides and alcoholates, such as sodium or potassium hydroxide, methylate, or ethylate, or fluorides, such as cesium fluoride or tetra-n-butyl-ammonium fluoride.

If desired, it is also possible to use in the reaction the β-carbolines that are substituted in the 9-position with a blocking group, such as the tosyl group. This blocking group is split off as described above during the working up of the reaction mixture or subsequently by treatment with alkali alcoholates.

If the compounds according to this invention are prepared by following process version (c), then the process as described by J. Lin, S. A. Lang, J. Org. Chem. 1980: 4857 can be utilized, for example, by first forming the enaminone which is cyclized, in general without being worked up, with hydroxylamine—O—sulfonic acid. The reaction is performed at room temperature up to 100° C. with or without addition of solvent. For the enaminone formation, dialkyl formamide dialkyl acetal or animal esters are utilized, for example. Cyclization can take place in protic solvents, such as alcohols, e.g. methanol, ethanol, propanol, etc., and is completed after 1–24 hours.

The preparation of the starting compounds is conventional or takes place according to known methods.

For example, the nitrile oxides are produced by splitting off hydrogen halide from the hydroxamic acid halogenides with bases, such as sodium or potassium alcoholates, trialkylamines, ethyldiisopropylamine, 1,8-diazabicyclo (5.4.0) undec-7-ene (DBU), or diazabicyclooctane at room temperature. The hydroxamic acid halogenides are obtained, for example, by reacting the corresponding oximes with N-bromo-succinimide, N-chlorosuccinimide, tert-butoxychlorite or sodium hypohalogenite in the previously recited aprotic solvents (R. Annunziata et al., J. Chem. Soc. Chem. Comm. 1987: 529, K. Larsen et al. Tetr. 1984: 2985).

Nitrile oxides can also be obtained by formal water cleavage from the corresponding nitro compounds by reaction with an acid chloride or aryl isocyanate in the presence of a base, such as trialkylamine or an alkali alcoholate in the aforementioned aprotic solvents at temperatures of −10° C. to 40° C. (K. Harada et al. Chem. Pharm. Bull. Jpn. 1980: 3296; H. Kawakami et al. Chem. Lett. 1987: 85).

Preparation of starting materials has been disclosed, for example, in EP-A No. 54,507, EP-A No. 218,541, EP-A No. 130,140, and EP-A No. 237,467.

Without further elaboration, it is believed that one skilled in the art can, using the preceding description, utilize the present invention to its fullest extent. The following preferred specific embodiments are, therefore, to be construed as merely illustrative, and not limitative to the remainder of the disclosure in any way whatsoever.

In the foregoing and in the following examples, all temperatures are set forth uncorrected in degrees Celsius and, unless otherwise indicated, all parts and percentages are by weight.

The entire texts of all applications, patents and publications, if any, cited above and below, and of corresponding applications German No. P 37 30 667.7 and Danish No. 4498/87 (the priority documents), are hereby incorporated by reference.

EXAMPLES

PREPARATION OF STARTING COMPOUNDS

6-Benzyloxy-4-methoxymethyl-β-carboline-3-carbaldehyde 15 ml of chlorotrimethylsilane and 48 ml of triethylamine are added to a suspension of 24.3 g (60 mmol) of 6-benzyloxy-4-methoxymethyl-β-carboline-3-carboxylic acid isopropyl ester in 250 ml of dry toluene. The reaction mixture is heated for one hour to 50° C. and then concentrated to half its volume. Thereafter the reaction mixture is cooled to −78° C. and, under nitrogen, 100 ml of DIBAL-H* (1-molar solution in toluene) is added within one-half hour; the mixture is stirred for another half hour at −78° C. Then the mixture is combined with 10 ml of ethanol and heated to room temperature; 200 ml of 0.5-molar sodium hydroxide solution and 200 ml of ethanol are added, and the mixture is stirred overnight. The precipitate is filtered off, washed with water, dried, and utilized in the subsequent reaction step without further purification.

* diisobutyl aluminum hydride

Analogously there is produced:
β-carboline-3-carbaldehyde.

6-Benzyloxy-4-methoxymethyl-β-carboline-3-carbaldehyde Oxime 13.5 g of 6-benzyloxy-4-methoxymethyl-β-carboline-3-carbaldehyde is dissolved in 150 ml of dry dimethyl formamide (DMF) and there are added thereto 6 g of hydroxylamine hydrochloride and a solution of 6 g of potassium hydroxide in 30 ml of ethanol. The reaction mixture is stirred for one hour at room temperature, filtered, and the residue washed with 2×20 ml of DMF. The DMF fraction is combined with 200 ml of ice water, the precipitate is filtered off, washed with water, and dried. Yield: 9.6 g.

The following compounds are produced analogously:
6-(2-pyrazinyloxy)-4-methoxymethyl-β-carboline-3-carbaldehyde oxime,
6-(4-chlorophenoxy)-4-methoxymethyl-β-carboline-3-carbaldehyde oxime,
6-(2-pyridyloxy)-4-methoxymethyl-β-carboline-3-carbaldehyde oxime,
6-methyl-4-methoxymethyl-β-carboline-3-carbaldehyde oxime,
6-(5-bromopyrid-2-yl)-4-methoxymethyl-β-carboline-3-carbaldehyde oxime,
6-benzyloxy-4-methyl-β-carboline-3-carbaldehyde oxime.

5-Benzyloxy-4-methoxymethyl-9-tosyl-β-carboline-3-carbaldehyde Oxime 500 mg of 5-benzyloxy-4-methoxymethyl-9-tosyl-β-carboline-3-carbaldehyde is heated in 15 ml of ethanol to 70° C., combined with 84 mg of hydroxylamine hydrochloride in 10 ml of ethanol and heated for 1.5 hours to 70° C. Then the mixture is concentrated to 5 ml, poured on 40 ml of water, and suctioned off. The residue (450 mg) is utilized after drying in the subsequent stage without further purification.

The following compounds are prepared analogously:
5-isopropoxy-4-methyl-9-tosyl-β-carboline-3-carbaldehyde oxime,
5-(4-chlorophenoxy)-4-methoxymethyl-9-tosyl-β-carboline-3-carbaldehyde oxime,
5-(2-pyrazinyloxy)-4-methoxymethyl-9-tosyl-β-carboline-3-carbaldehyde oxime,
5-(5-bromo-2-pyridinyloxy)-4-methoxymethyl-9-tosyl-β-carboline-3-carbaldehyde oxime,
6,7-dimethoxy-4-ethyl-9-tosyl-β-carboline-3-carbaldehyde oxime

3-Acetyl-5-benzyloxy-4-methoxymethyl-9-tosyl-β-carboline 3.3 g of 5-benzyloxy-4-methoxymethyl-9-tosyl-β-carboline-3-carboxylic acid ethyl ester is suspended in 25 ml of absolute tetrahydrofuran (THF) and cooled to −60° C. under an N$_2$ atmosphere. To this suspension is added dropwise 5.2 ml of a 1.5-molar ethereal methyllithium solution and the mixture is stirred for another 2 hours at −60° C. After heating to room temperature, the reaction mixture is combined with saturated ammonium chloride solution and extracted with ethyl acetate. The crude product is purified by chromatography on silica gel with toluene+ethyl acetate in a ratio of 95:5.

3-Acetyl-6-benzyloxy-4-methoxymethyl-β-carboline

Under an N$_2$ atmosphere, 45 mmol of n-butyl-lithium is added dropwise within 10 minutes to 3.70 g (22 mmol) of methanesulfine-p-toluidide in 100 ml of dry THF at −78° C. To this mixture is added 5.58 g (10 mmol) of 6-benzyloxy-4-methoxymethyl-9-tosyl-β-carboline-3-carboxylic acid isopropyl ester, dissolved in 50 ml of dry THF. The reaction mixture assumes a dark-blue color. The mixture is stirred for one hour at −78° C., poured into water, and extracted with ether. The ether is drawn off and the remaining oil is dissolved in 100 ml of methanol. Then 5 g of KOH is added and the mixture agitated under reflux for one hour. After cooling, ice water is added and the precipitate is filtered off. Yield: 3.5 g.

The crude product is purified by means of chromatography on silica gel with ethyl acetate. Yield: 2.80 g.

EXAMPLE 1

6-Benzyloxy-3-(3-isoxazolyl)-4-methoxymethyl-β-carboline 0.55 g (1.5 mmol) of 6-benzyloxy-4-methoxymethyl-β-carboline-3-carbaldehyde oxime is dissolved in 30 ml of dry DMF and combined with 0.3 g (1.7 mmol) of N-bromosuccinimide (dissolved in 5 ml of DMF). The reaction mixture is stirred for 10 minutes at room temperature and then 1.5 eq. of trimethylsilylacetylene and 1 ml of triethylamine are added. After 4 hours of agitation at room temperature, 5 ml of 1-molar sodium hydroxide solution is added and subsequently agitation is continued for another hour. The solution is poured into ice water and extracted with ethyl acetate. The organic phase is dried over magnesium sulfate and the solvent drawn off. The resultant product is purified by column chromatography on silica gel with ethyl acetate as the eluent. Melting point: 123°–126° C.

EXAMPLE 2

6-Benzyloxy-3-(5-ethoxy-3-isoxazolyl)-4-methoxymethyl-β-carboline 1.1 g (3.0 mmol) of 6-benzyloxy-4-methoxymethyl-β-carboline-3-carbaldehyde oxime is dissolved in 40 ml of dry DMF and combined with 0.56 g (3.1 mmol) of N-bromosuccinimide (dissolved in 5 ml of DMF). The reaction mixture is stirred for 15 minutes at room temperature and then combined with 1.5 eq. of ethoxyacetylene and 2 ml of triethylamine. The reaction mixture is agitated overnight at room temperature, then poured on ice water and extracted with ethyl acetate. The organic phase is dried over magnesium sulfate, filtered, the solvent drawn off, and the residue purified by column chromatography on silica gel with ethyl acetate. Melting point: 139°–140° C.

The following compounds are produced analogously:
6-Benzyloxy-3-(5-hydroxymethyl-3-isoxazolyl)-4-methoxymethyl-β-carboline with hydroxymethylacetylene; melting point: 220°–221° C.,
6-benzyloxy-3-(5-methoxymethyl-3-isoxazolyl)-4-methoxymethyl-β-carboline with methoxymethylacetylene; melting point: 89°–90° C., With propargylic acid, the following compounds are obtained with the use of column chromatography:
6-benzyloxy-3-(5-carbethoxy-3-isoxazolyl)-4-methoxymethyl-β-carboline; melting point: 202°–203° C., and
6-benzyloxy-3-(4-carbethoxy-3-isoxazolyl)-4-methoxymethyl-β-carboline; melting point: 145°–146° C.
6-Benzyloxy-3-(4-carbethoxy-4,5-dihydro-3-isoxazolyl)-4-methoxymethyl-β-carbonile with acrylic acid ethyl ester; melting point: 183° C., 6-benzyloxy-3-(4-carbethoxy-4,5-dihydro-4-methyl-3-isoxazolyl)-4-methoxymethyl-β-carboline with methacrylic acid ethyl ester; melting point: 187°–189° C.,
6-benzyloxy-3-(5-ethoxy-4,5-dihydro-3-isoxazolyl)-4-methoxymethyl-β-carboline with vinyl ethyl ether; melting point: 149°–150° C.,
6-benzyloxy-3-(5-methyl-3-isoxazolyl)-4-methoxymethyl-β-carboline; melting point: 160°–162° C.
6-(2-pyrazinyloxy)-3-(5-methoxymethyl-3-isoxazolyl)-4-methoxymethyl-β-carboline; melting point: 184° C.
6-methyl-3-(5-methyl-3-isoxazolyl)-4-methoxymethyl-β-carboline; melting point: 178° C.,
6-methyl-3-(5-methoxymethyl-3-isoxazolyl)-4-methoxymethyl-β-carboline; melting point: 160° C.,
6-(5-bromopyrid-2-yl)oxy-4-methoxymethyl-3-(3-isoxazolyl)-β-carboline; melting point: 203° C.,
6-(5-bromopyrid-2-yl)oxy-3-(5-methyl-3-isoxazolyl)-4-methoxymethyl-β-carboline; melting point: 197°–198° C.
6-(5-bromopyrid-2-yl)oxy-3-(5-methoxymethyl-3-isoxazolyl)-4-methoxymethyl-β-carboline; melting point: 164° C.,
6-4-methoxymethyl-3-(5-isopropyl-3-isoxazolyl)-β-carboline,
6-benzyloxy-4-methoxymethyl-3-(5-cyclopentyl-3-isoxazolyl)-β-carboline,
6-benzyloxy-4-methoxymethyl-3-(5-ethoxymethyl-3-isoxazolyl)-β-carboline,
6-benzyloxy-4-methyl-3-(5-ethoxymethyl-3-isoxazolyl)-β-carboline.

EXAMPLE 3

6-Bromo-3-(3-isoxazolyl)-β-carboline 1.05 g (5 mmol) of β-carboline-3-carbaldehyde oxime is suspended in 50 ml of dry THF and combined at 0° C. with 1.8 g of N-bromosuccinimide in 20 ml of dry THF. The reaction mixture is heated to room temperature, stirred for 95 hours, and combined with 1.5 eq. of trimethylsilylacetylene and 2 ml of triethylamine. The mixture is further stirred overnight, poured on ice water, and extracted with ether. The organic phase is dried over magnesium sulfate, filtered, and the solvent drawn off. The remaining oil is dissolved in 10 ml of DMF and combined with 10 ml of sodium hydroxide solution (1-molar). The reaction mixture is stirred overnight at room temperature, poured on water, and extracted with ethyl acetate. The resultant product is purified by column chromatography with ethyl acetate as the eluent. Melting point: 292°–293° C.

EXAMPLE 4

5-Benzyloxy-4-methoxymethyl-3-(3-isoxazolyl)-β-carboline 103 mg of 5-benzyloxy-4-methoxymethyl-9-tosyl-β-carboline-3-carbaldehyde oxime is combined in 5 ml of methylene chloride with 22 mg of N-chlorosuccinimide and agitated for one hour at room temperature. Subsequently 30 mg of trimethylsilylacetylene and 0.13 ml of triethylamine are added and the mixture stirred for 2 hours at room temperature. The mixture is then combined with 1 ml of 1N sodium hydroxide solution and agitated for one hour at room temperature, poured on 25 ml of water, extracted with 25 ml of methylene chloride, and the organic phase is dried, filtered, and concentrated. The residue is refluxed for 1.5 hours in 15 ml of methanol with 54 mg of sodium methylate. After concentration, the mixture is taken up in 25 ml of water and extracted with ethyl acetate. After drying and filtration, the organic phase is concentrated and the residue is chromatographed over silica gel with toluene+ethyl acetate in a ratio of 1:1 as the eluent.

EXAMPLE 5

5-Benzyloxy-4-methoxymethyl-3-(5-methoxymethyl-3-isoxazolyl)-β-carboline

At room temperature under a protective gas, 1.4 ml of sodium hypochlorite solution is added dropwise to 155 mg of 5-benzyloxy-4-methoxymethyl-9-tosyl-β-carboline-3-carbaldehyde oxime hydrochloride in 6 ml of absolute tetrahydrofuran. The mixture is stirred until the oxime has disappeared (TLC control) for one hour at room temperature, then 210 mg of methylpropargyl ether is added dropwise and the mixture is agitated overnight at room temperature. After the solvent has been removed by distillation, the mixture is distributed in ethyl acetate/water, and the organic phase is dried over magnesium sulfate, filtered, and concentrated. The residue is dissolved in 8 ml of methanol, combined with 54 mg of sodium methylate, and heated to reflux for one hour. After concentration and distribution in ethyl acetate/concentrated sodium chloride solution, the organic phase is dried, filtered, and concentrated. The residue is chromatographed over silica gel with toluene+ethyl acetate in a ratio of 1:1. The corresponding fractions are combined and crystallized from ethyl acetate, thus obtaining 70 mg, melting point 133°–135° C. (ethyl acetate).

The following compounds are produced analogously:
5-(4-chlorophenoxy)-4-methoxymethyl-3-(5-methoxymethyl-3-isoxazolyl)-β-carboline; melting point 176°–177° C. (isopropanol),
5-isopropoxy-4-methyl-3-(5-methoxymethyl-3-isoxazolyl)-β-carboline,
6,7-dimethoxy-4-ethyl-3-(5-methoxymethyl-3-isoxazolyl)-β-carboline,
5-(2-pyrazinyloxy)-4-methoxymethyl-3-(5-methoxymethyl-3-isoxazolyl)-β-carboline,
5-(5-bromo-2-pyridinyloxy)-4-methoxymethyl-3-(5-methoxymethyl-3-isoxazolyl)-β-carboline.

EXAMPLE 6

6-Benzyloxy-3-(3-methyl-5-isoxazolyl)-4-methoxymethyl-β-carboline 340 mg of nitroethane is combined in 20 ml of dry dimethylacetamide with 4.5 ml of a methanolic 1N sodium methylate solution and cooled in an ice bath to 5° C. To this mixture are added in succession 0.32 ml of acetyl chloride and 510 ml of 6-benzyloxy-4-methoxymethyl-3-ethynyl-β-carboline.

After 16 hours of agitation at room temperature, another 3 equivalents of methanolic 1N sodium methylate solution, nitroethane and acetyl chloride are added and again the mixture is stirred for 16 hours at room temperature. This addition is repeated, and after 3 days in total, 100 ml of water is added and the mixture is once again stirred overnight at room temperature. The reaction mixture is extracted with ethyl acetate. The organic phase is separated, dried, filtered, and concentrated.

After chromatography over silica gel with ethyl acetate, 130 ml of 6-benzyloxy-3-(3-methyl-5-isoxazolyl)-4-methoxymethyl-β-carboline is obtained, melting point 202°–203° C.

EXAMPLE 7

6-Benzyloxy-4-methoxymethyl-3-(5-isoxazolyl)-β-carboline

At 100° C., 500 mg of 3-acetyl-6-benzyloxy-4-methoxymethyl-β-carboline is stirred overnight in 5 ml of N,N-dimethylformamide diethylacetal. After concentration by evaporation, the mixture, without further purification, is taken up in 20 ml of absolute ethanol, combined with 600 mg of hydroxylamine-O-sulfonic acid in 5 ml of methanol, and stirred for 5 hours at room temperature. After neutralization with triethylamine, the reaction mixture is stirred overnight, introduced into water, and extracted with ethyl acetate; the organic phase is dried over magnesium sulfate and concentrated under vacuum. After chromatography over silica gel with acetone:triethylamine in a ratio of 10:1 as the eluent, 130 mg of 6-benzyloxy-4-methoxymethyl-3-(5-isoxazolyl)-β-carboline is obtained, melting point 125°–126° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

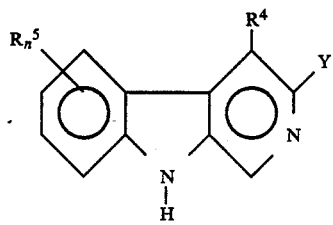

wherein
Y is

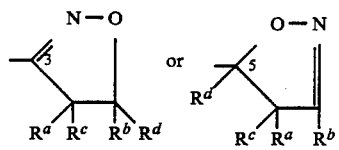

$R^a$ and $R^b$ are identical or different, and each is hydrogen, $C_{1-6}$-alkoxy, $C_{3-7}$-cycloalkyl, phenyl, $C_{1-6}$-alkyl, $C_{1-6}$-alkoxycarbonyl, $C_{1-6}$-alkyl substituted by OH, $C_{1-6}$-alkoxy, phenyl or halogen;

$R^c$ and $R^d$ are identical or different, and each is hydrogen or $C_{1-6}$-alkyl or jointly they form an additional C—C bond;

$R^4$ is hydrogen, $C_{1-6}$-alkyl or $C_{1-6}$-alkoxy-$C_{1-6}$-alkyl; n is 1 or 2;

$R^5$ is hydrogen, halogen, $OR^6$, $NR^7R^8$ or $CHR^9R^{10}$; with the proviso that, if $R^4$ and $R^5$ are hydrogen, Y is not 3-methyl-isoxazole-5-yl;

$R^6$ is $C_{1-6}$-alkyl, $C_{3-7}$-cycloalkyl or $C_{6-10}$-aralkyl, $C_{6-10}$-aryl, $C_{6-10}$-heteroaryl having 5- or 6-ring members and 1 or 2 hetero atoms of N, S or O;

$C_{6-10}$-aralkyl substituted once or twice in the aryl portion by halo, nitro, cyano, $C_{1-4}$-alkyl or $C_{1-4}$-alkoxy; $C_{6-10}$-aryl substituted once or twice in the aryl portion by halo, nitro, cyano, $C_{1-4}$-alkyl or $C_{1-4}$-alkoxy, or said heteroaryl group substituted once, twice or three times by halo, nitro, cyano, $C_{1-4}$-alkyl or $C_{1-4}$-alkoxy;

$R^7$ and $R^8$ are identical or different, and each is hydrogen, $C_{1-6}$-alkyl, $C_{3-6}$-alkenyl, or jointly with the nitrogen form a saturated heterocyclic 5- or 6-membered ring which optionally can contain one additional hetero atom, N, O or S;

$R^9$ is hydrogen or $C_{1-6}$-alkyl;

$R^{10}$ is hydrogen, $C_{1-6}$-alkyl, $OR^{11}$ or $NR^{12}R^{13}$ $R^{11}$ is $C_{1-6}$-alkyl, $R^{12}$ and $R^{13}$ are identical or different and each is hydrogen, $C_{1-6}$-alkyl or jointly with the nitrogen atom form a saturated heterocyclic 5- or 6-membered ring optionally containing one additional hetero atom, N, O or S.

2. 6-Benzyloxy-3-(3-isoxazolyl)-4-methoxymethyl-β-carboline;
6-benzyloxy-3-(5-ethoxy-3-isoxazolyl)-4-methoxymethyl-β-carboline;
6-benzyloxy-3-(5-hydroxymethyl-3-isoxazolyl)-4-methoxymethyl-β-carboline;
6-benzyloxy-3-(5-methoxymethyl-3-isoxazolyl)-4-methoxmethyl-β-carboline;
6-benzyloxy-3-(5-ethoxy-4,5-dihydro-3-isoxazolyl)-4-methoxymethyl-β-carboline;
6-benzyloxy-3-(5-methyl-3-isoxazolyl)-4-methoxymethyl-β-carboline;
6-benzyloxy-4-methoxymethyl-3-(3-methyl-5-isoxazolyl)-β-carboline;
5-benzyloxy-4-methoxymethyl-3-(5-methoxymethyl-3-isoxazolyl)-β-carboline;
5-phenoxy-4-methoxymethyl-3-(3-isoxazolyl)-β-carboline, 5-(4-chlorophenoxy)-3-(5-methoxymethyl-3-isoxazolyl)-4-methoxymethyl-β-carboline;
6-(2-pyrazinyloxy)-4-methoxymethyl-3-(5-methoxymethyl-3-isoxazolyl)-β-carboline;
6-(5-bromopyrid-2-yl)oxy-4-methoxymethyl-3-(5-methyl-3-isoxazolyl)-β-carboline; each a compound of claim 1.

3. A compound of claim 1, wherein Y is

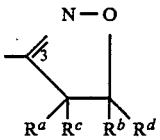

4. A compound of claim 1, wherein Y is

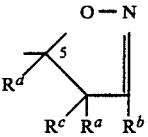

5. A compound of claim 1, wherein $R^4$ is $C_{1-6}$-alkoxy-$C_{1-6}$-alkyl.

6. A compound of claim 1, wherein n=1.

7. A compound of claim 6, wherein $R^5$ is in the 5-position.

8. A compound of claim 6, wherein $R^5$ is in the 6-position.

9. A compound of claim 1, wherein $R^5$ is $OR^6$ and wherein $R^6$ is $C_{6-10}$-aryl.

10. A compound of claim 1, wherein $R^5$ is $OR^6$ and wherein $R^6$ is $C_{6-10}$-aralkyl.

11. A compound of claim 1, wherein $R^5$ is $OR^6$ and wherein $R^6$ is $C_{6-10}$-aryl substituted once or twice in the aryl portion by halo, nitro, cyano, $C_{1-4}$-alkyl or $C_{1-4}$-alkoxy.

12. A compound of claim 1, wherein $R^5$ is $OR^6$ and wherein $R^6$ is $C_{6-10}$-heteroaryl having 5- or 6-ring members and 1 or 2 heteratoms of N, S or O.

13. A compound of claim 1, wherein $R^5$ is $OR^6$ and wherein $R^6$ is $C_{6-10}$-heteroaryl having 5- or 6-ring members and 1 or 2 heteroatoms of N, S or O, substituted once, twice or three times by halo, nitro, cyano $C_{1-4}$-alkyl or $C_{1-4}$-alkoxy.

14. A pharmaceutical composition, comprising an effective amount of a compound of claim 1 and a pharmaceutically acceptable carrier.

15. A pharmaceutical composition of claim 14, wherein said amount is 0.05 to 100 mg.

16. A method of treating epilepsy, comprising administering an effective amount of a compound of claim 1.

17. A method of treating anxiety, comprising administering an effective amount of a compound of claim 1.

* * * * *